US006783648B1

(12) United States Patent
Anderson et al.

(10) Patent No.: US 6,783,648 B1
(45) Date of Patent: Aug. 31, 2004

(54) METHOD AND APPARATUS FOR UNLOADING GELS FROM ISOELECTRIC GEL TUBES

(75) Inventors: N. Leigh Anderson, Washington, DC (US); Jack Goodman, Lusby, MD (US)

(73) Assignee: Large Scale Proteomics Corporation, Germantown, MD (US)

( * ) Notice: Subject to any disclaimer, the term of this patent is extended or adjusted under 35 U.S.C. 154(b) by 812 days.

(21) Appl. No.: 09/654,131

(22) Filed: Sep. 1, 2000

(51) Int. Cl.[7] .............................................. B01D 57/02
(52) U.S. Cl. ....................... 204/462; 204/459; 204/465; 204/466; 204/467; 204/606; 204/610; 204/613; 204/615; 204/616; 204/618; 222/162; 222/325; 222/326
(58) Field of Search ................................ 204/456, 459, 204/462, 465, 466, 467, 606, 610, 613, 615, 616, 618; 222/162, 325, 326

(56) References Cited

U.S. PATENT DOCUMENTS 4,279,361 A * 7/1981 Chung .......................... 222/1
4,305,799 A * 12/1981 Schwarz et al. ............ 204/455
5,292,420 A * 3/1994 Nakanura ................... 204/613

* cited by examiner

*Primary Examiner*—Nam Nguyen
*Assistant Examiner*—John S. Starsiak, Jr.
(74) *Attorney, Agent, or Firm*—John C. Robbins; John E. Tarcza; Garrett V. Davis

(57) ABSTRACT

An apparatus for expressing and unloading an isoelectric focusing gel from an electrophoresis gel tube includes a first support for supporting the gel tube, a plunger rod and a second support for supporting the plunger rod. The first support is mounted on a movable carriage and is moved toward the second support so that the gel tube slides onto the plunger rod to unload the gel from the gel tube. A plurality of gel tubes can be mounted in a rack and the rack coupled to the first support. The first support preferably includes a plurality of openings oriented with the gel tubes for guiding a respective plunger rod through the axial passage of the gel tubes. In preferred embodiments, the second support supporting the plunger rods is substantially stationary while the first support moves toward the second support so that the gel tubes slide onto the plunger rods. A plunger member such as a rubber ball is positioned in the axial passage of the gel tubes between the gel and the plunger rod to unload the gel in a substantially uniform manner without tearing or breaking the gel.

59 Claims, 13 Drawing Sheets

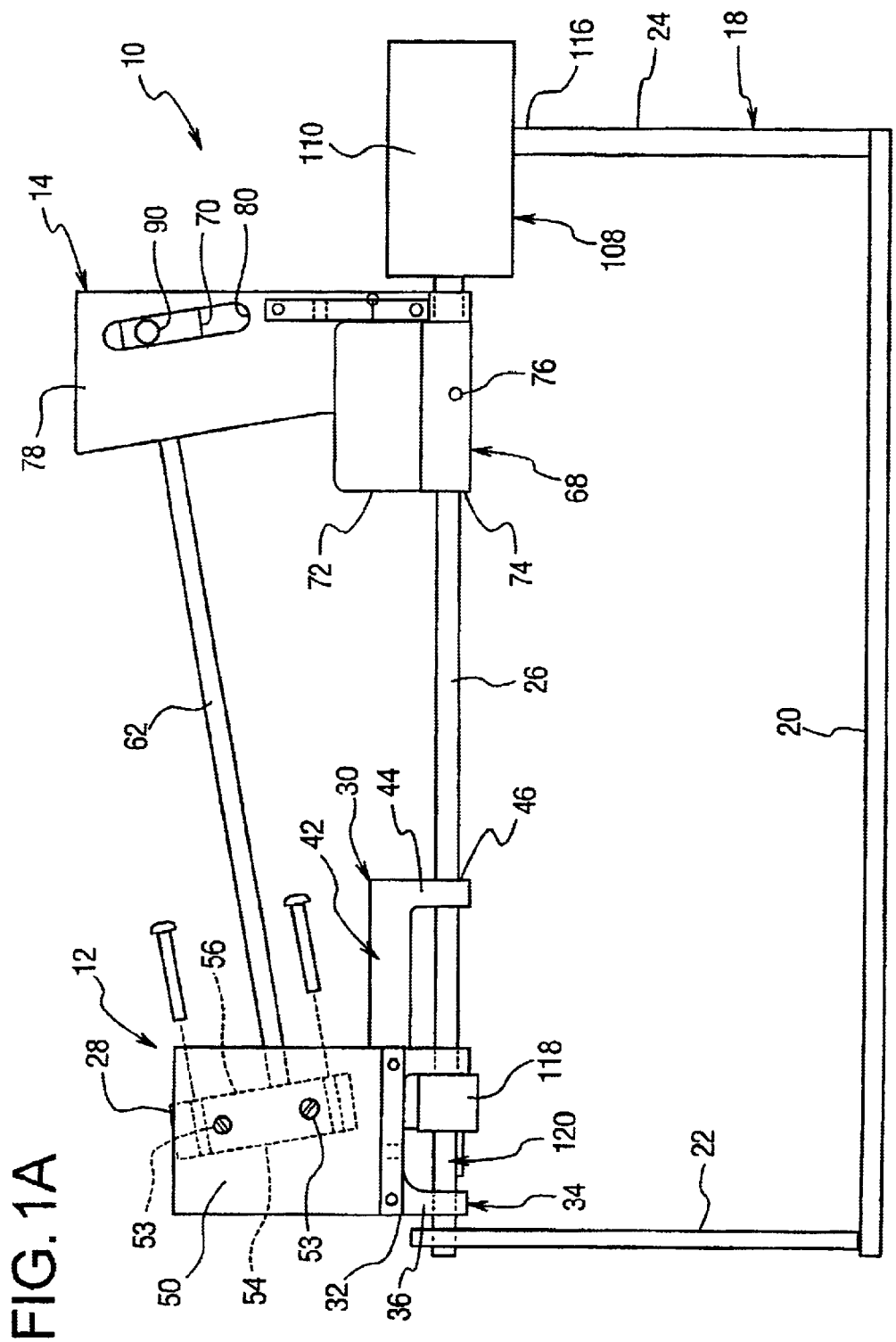

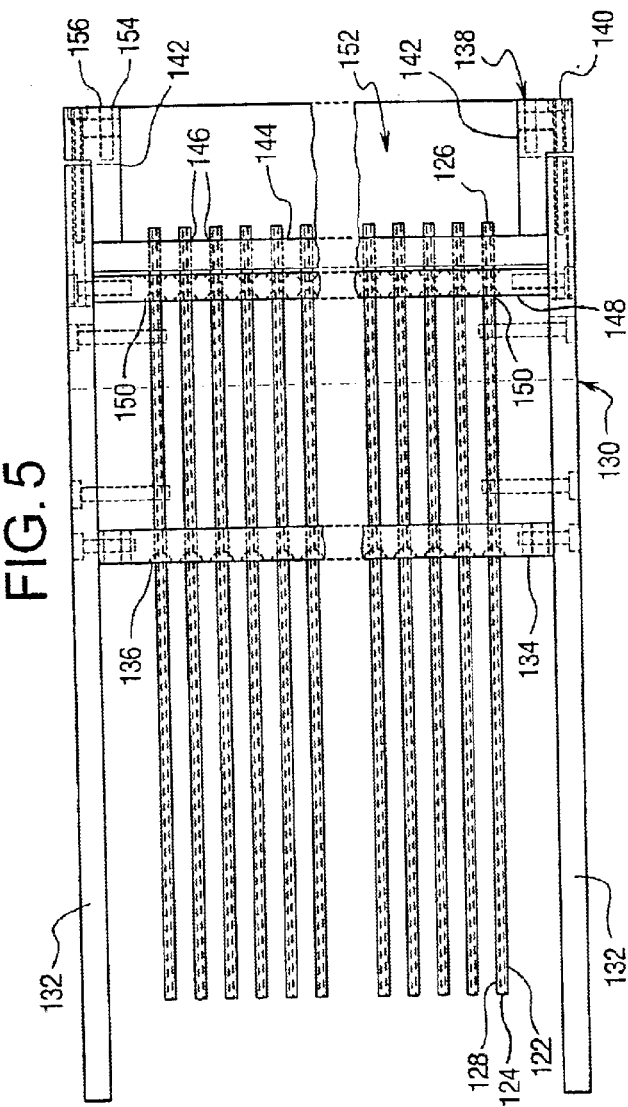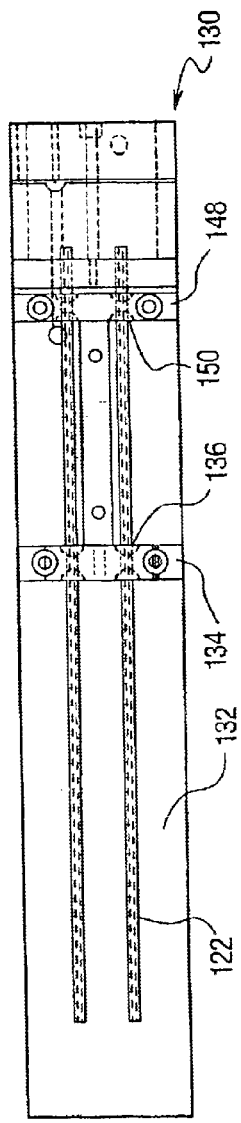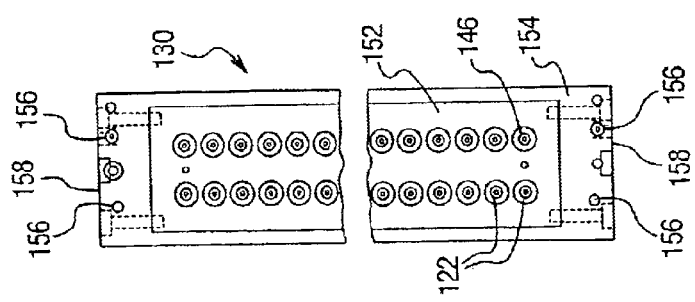

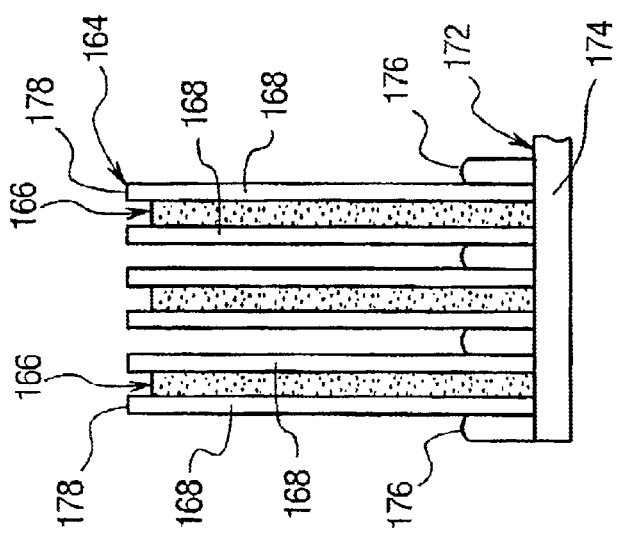
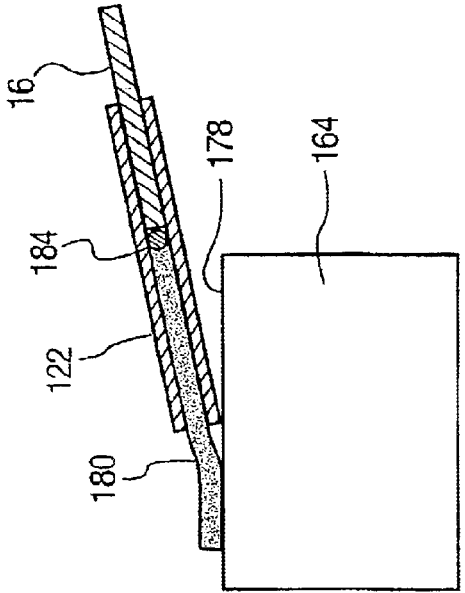

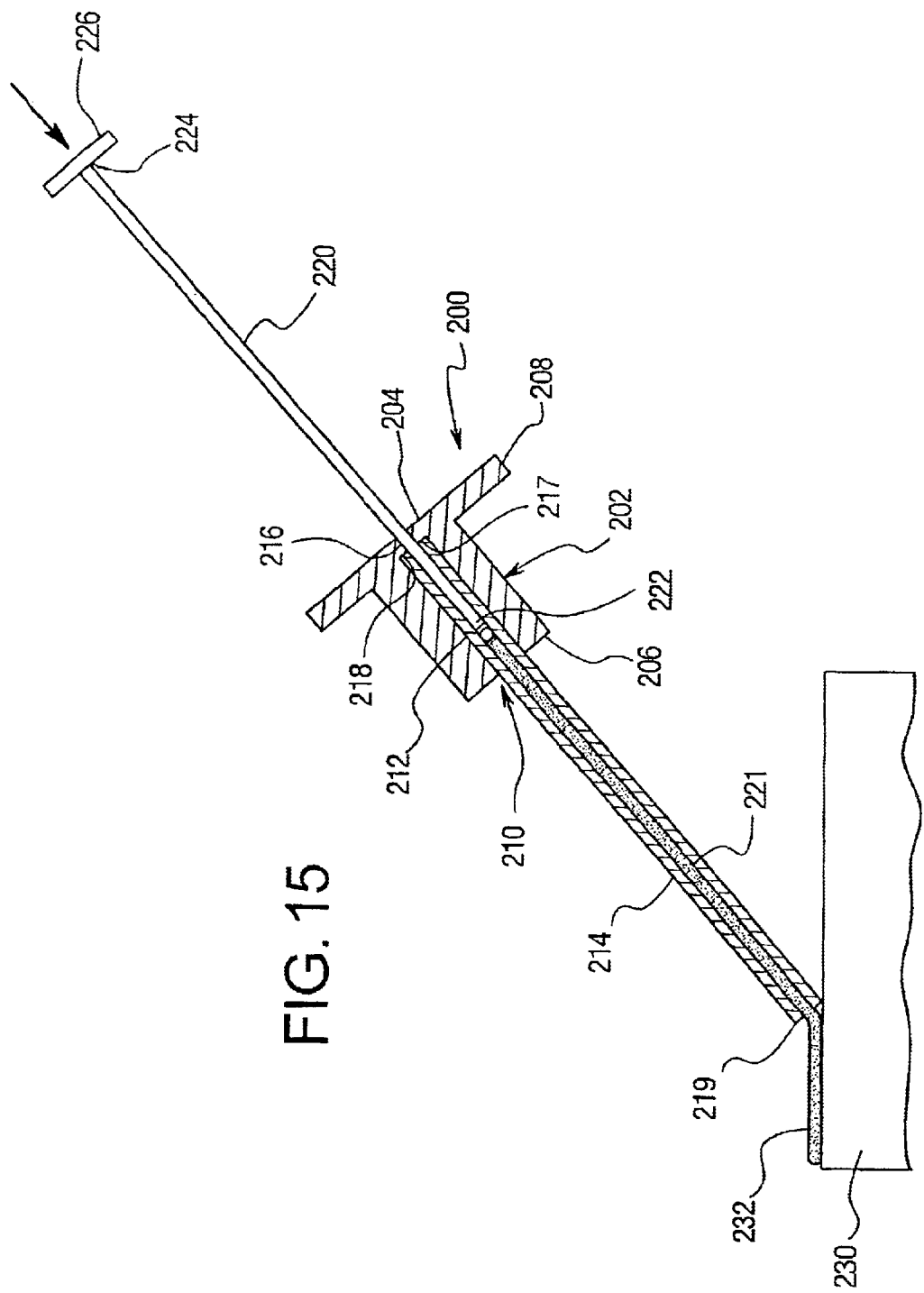

METHOD AND APPARATUS FOR UNLOADING GELS FROM ISOELECTRIC GEL TUBES

FIELD OF THE INVENTION

The present invention is directed to a method and apparatus for automatically unloading an isoelectric focusing gel from a tube onto a surface, and particularly a gel slab. More particularly, the invention is directed to a method and apparatus for unloading a gel from a tube as a continuous bead.

BACKGROUND OF THE INVENTION

Genomes provide the sequence information required to construct proteins that are the working parts of living cells. Genomes and genes are linear constructs composed of four different nucleotides arranged in triplet condons that specify the order and identity of the approximately 20 different amino acids that make up proteins. The nucleic acids are chemically very similar, and are arranged in very long contiguous sequences with intervening non-coding regions. For analysis, nucleic acids must be cut up into fragments of tractable length using shearing forces or restriction enzymes which cut the nucleic acid at specific known sites.

Proteins are made of amino acid subunits that have a range of different isoelectric points, molecular weights, and solubility or hydrophobicity characteristics. The synthesized peptides have exactly defined lengths, and roll up or are assembled into proteins of well defined molecular weights. The estimated 100,000 different primary proteins in man have a range of charge densities and isoelectric points, solubilities, and surface characteristics not found in nucleic acids. Further, proteins have a range of surface conformations which mediate specific interactions between proteins, between proteins and nucleic acids, and, in the form of enzymatically active sites, between low molecular weight metabolites, and all the various types of macromolecules found in cells and foodstuffs. Proteins are the molecular machines that carry out the panoply of syntheses, disassemblies and degradations, immunochemical defense reactions, and paratactic interactions that underlie the assembly of membranes and subcellular organelles.

There is a need for analytical methods that allow a large fraction of the total number of proteins present in a cell or tissue to be detected and quantitated. The quantitative analysis of large sets of proteins that have such a wide variety of functions, sizes, conformation, activities, solubilities, and charge characteristics is both a centrally important challenge, and an exceedingly difficult problem. The problem is rendered even more difficult by the requirement that analysis detecting thousands of proteins per analyses be done in parallel on relatively large numbers of samples in a reasonable time to do experimental toxicological and pharmacological studies.

The electrophoretic mobility of a non-denatured protein is a function of the surface charges of either the monomeric protein or the sum of the surface charges of the subunits, and these are generally used under rate-zonal conditions, i.e., under conditions where the proteins move through a gel or other support at one pH. The distance traveled is a function of the charge to mass ratio, and a function of electrophoresis time. Second dimension separations are done in gradient gels of decreasing pore size such that proteins move until movement essentially ceases as the protein reach pore sizes that prevent further movement. Experimental attempts to develop two dimensional methods based on these parameters using non-denaturing conditions have not yielded the resolution required.

Two-dimensional methods involving denaturing conditions have been explored and widely adopted. The initial separation is done in concentrated urea in the presence of ampholytes which are a heterogeneous mixture of synthetic polymers having wide variation in the ratio of acidic to basic groups. When these are subjected to an electrical field in a gel, the ampholytes sort themselves out into a continuous series based on the isoelectric point. Proteins move along the gel until they reach their own isoelectric point and stop. Further, since the proteins are denatured and unrolled, their isoelectric points reflect the sum of all of the charged groups in the protein, whether previously external or internal in the native state. The isoelectric point determination in such a separation can be calculated from the amino acid composition of the protein, and is a valuable parameter for protein classification.

The second dimensional separation is based on the length (and hence the mass) of the unrolled denatured protein and takes place in the following way. Proteins from the isoelectric separation are exposed to a highly charged detergent which has attached the longest paraffin chain which will remain extended in solution, and not fold back on itself. Sodium dodecyl sulfate (SDS) is the detergent of choice, and in solution will uniformly coat unrolled polypeptide chains, and attach to them by hydrophobic linkages, leaving the highly charged sulfate groups on the surface. The result is particles of approximately rod shape having approximately equal charge-to-mass ratios. Particles having equal charge-to-mass ratios move at the same rate in electrical fields, so that all proteins covered with SDS should have equal mobility in solution. However, if electrophoresis of such particles is done in a microporous gel, then larger particles will be retarded relative to smaller ones.

In practice, the resolutions of these two separate methods are quite high. At least 150 proteins can be resolved from a suitable mixture by isoelectric focusing, and an equal number resolved from a suitable protein mixture by SDS electrophoresis. If the two processes can be mated together in a two-dimensional array, the final resolution should be the product of the resolution of the two methods separately, i.e., $150^2$ or 22,500. Experimentally, as many as 5,000 proteins have been resolved in large two-dimensional electrophoresis gels, and the theoretical resolution of current electrophoresis as calculated from spot sizes, and the number of spots which could theoretically be packed into the gel area used is around 30,000.

It is quite evident that a key step in the high-resolution two-dimensional electrophoresis technique using isoelectric focusing followed by SDS electrophoresis in the second dimension is mating the two methods together without the loss of resolution inherent in collecting and separately analyzing fractions.

Experimentally, isoelectric focusing is done under temperature controlled conditions in glass tubes (ISO tubes) having an internal diameter of approximately 0.5–2 mm, and approximately 30 cm long. ISO tubes are then attached to a small syringe full of water or buffer solution, and the gels extruded by hand along the top of a second-dimension gel cast between two glass plates. An empty space is typically formed between the top of the gel and the top of the plates. The gels are carefully extruded into this space by a double movement in which the syringe plunger is moved to extrude the gel as the ISO tube containing the gel is moved laterally along the top of the second dimension gel. This movement requires considerable skill, and many gels are broken as they are extruded and moved into place. It is further evident that different portions of the extruded gels may be stretched differently, causing distortion in the final 2D pattern. A further difficulty is that this step is the most variable and time consuming one in present programs aimed at automating the entire 2D process, in which batches of analyses varying from 10–60 are run in parallel. The 2D protein analysis has become a core analytical method in pharmacology and toxicology, and mass spectrometric analysis and identification of proteins in spots from 2D gels has become routine and essential. Accordingly, there is a continuing need in the industry for a system and method for automatically unloading large sets of gels from isoelectric focusing gel tubes directly onto second dimension gels with minimal distortion or breakage.

SUMMARY OF THE INVENTION

The present invention is directed to a method and apparatus for unloading a gel from a tube. More particularly, the invention is directed to a method and apparatus for the unloading of an isoelectric gel from a gel tube onto a gel slab or other work surface.

Accordingly, a primary object of the invention is to provide a method and apparatus for unloading a substance, and particularly a gel, from a tube substantially without distortion of the substance.

A further object of the invention is to provide a method and apparatus for unloading an isoelectric gel from a gel tube in a substantially uniform and controlled manner.

Another object of the invention is to provide an apparatus for removing a gel body from a cylindrical tube substantially without compressing or elongating the gel body.

A further object of the invention is to provide an apparatus for removing a substance from a cylindrical tube onto a surface by passing a plunger rod through the tube at a substantially uniform speed.

A further object of the invention is to provide a method and apparatus for unloading a gel from a cylindrical tube using a plunger rod mounted in a fixed position where one end of the tube slides onto the plunger rod to discharge the gel from the opposite end of the tube.

Another object of the invention is to provide a method and apparatus for unloading a substance from a tube at a controlled rate where the tube is moved along the surface at a controlled rate to discharge of the gel from the tube and uniformly onto a surface.

A further object of the invention is to provide a method and apparatus for discharging a gel from a tube using a flexible plunger member having a diameter greater than an internal diameter of the tube where the plunger member is fitted into one end of the tube and pushed along the length of the tube.

Still another object of the invention is to provide an apparatus for unloading a gel from a tube onto a surface where the apparatus moves the tube across the surface at a substantially constant speed and constant angle with respect to the direction of movement of the tube.

A further object of the invention is to provide an apparatus for unloading a gel from a plurality of tubes where the apparatus includes a movable support for the tubes, a plunger rod associated with each tube, and a stationary support coupled to one end of the rods, where the movable support moves toward the stationary support to slide one end of the tubes over the respective plunger rod and to unload the gel from the opposite end of the tubes.

The objects and advantages of the invention are basically attained by providing an apparatus for unloading a substance from a tube. The apparatus comprises a first support assembly for supporting a plurality of tubes, each of the tubes having an axial passage, a first open end and a second open end, the first end of the tube being coupled to the first support; a second support spaced from the first support; a plurality of plungers having a first end coupled to the second support and a second end axially aligned with an axial passage of a respective tube; and a drive assembly for moving the first support along a linear path toward the second support, whereby the tubes slide onto the respective plunger to unload the substance from the second end of the tubes.

The objects and advantages of the invention are further attained by providing an apparatus for unloading a substance from a tube onto a surface. The apparatus comprises a first support having a first side and a second side with at least one aperture extending through the carriage between the first side and the second side and having a removable carriage; a tube support member for supporting at least one tube containing the substance, the tube support member being coupled to the first side of the first support so that the tube is aligned with the at least one aperture; a second support spaced from the first support; at least one plunger rod having a first end coupled to the second support and a second end received in the at least one aperture of the first support; and a drive assembly for moving the carriage, in a linear path toward the second support whereby the plunger rod passes through the tube to unload the substance onto a surface.

The objects and advantages of the invention are still further attained by providing an apparatus for unloading an electrophoresis gel from an electrophoresis gel tube onto a gel slab. The apparatus comprises a first support having a first side and a second side with a plurality of apertures extending through the first support between the first side and the second side and having a movable carriage; a gel tube member having a plurality of electrophoresis gel tubes containing the electrophoresis gel, the gel tubes having a first end coupled to the gel tube support member and a second end spaced from the first support member, the gel tube support member being coupled to the first side of the first support so that the tubes are aligned with a respective aperture; a second support spaced from the first support; a plurality of plunger rods having a first end coupled to the second support and a second end received in the at least one aperture of the first support; a plurality of vertically oriented gel slabs having a top edge aligned with a respective gel tube; and a drive assembly for moving the carriage toward the second support whereby the plunger rod passes through the tube to unload the electrophoresis gel onto the top edge of the gel slabs.

The objects and advantages of the invention are yet further attained by providing an apparatus for unloading a gel from an isoelectric focusing gel tube. The apparatus comprises a housing having a first end, a second end opposite the first end and a side wall,. The housing has an axial passage extending between the first and second ends. The axial passage has a first open end at the first end of the housing and a second open end at the second end of the housing. A plunger rod has a first end positioned in the first open end of the axial passage of the housing. A gel tube has an axial bore containing an isoelectric focusing gel. The gel tube has a substantially cylindrical shape with a first open axial end and a second open axial end. The first open axial end of the gel tube is positioned in the second open end of the axial passage. A resilient plunger member is positioned between the first end of the plunger rod and the gel within the gel tube. The resilient plunger member has an outer dimension to fit within the bore of the gel tube.

The objects and advantages of the invention are still further attained by providing a method of unloading an isoelectric focusing gel from a gel tube. The method comprises providing a gel tube having an axial bore containing an isoelectric focusing gel. The gel tube has a first open axial end and a second open axial end. The first end of the gel tube is coupled to a first end of an unloading assembly. The unloading assembly has a flexible plunger member aligned with the first open axial end of the gel tube and a reciprocating plunger rod aligned with the plunger member and the first open axial end of the gel tube. The plunger rod moves against the plunger member and forces the plunger member and the first end of the plunger rod through the axial passage of the gel tube to unload the gel.

The objects, advantages and salient features of the invention will become apparent to one skilled in the art in view of the following detailed description of the invention in conjunction with the annexed drawings which form a part of this original disclosure.

BRIEF DESCRIPTION OF THE DRAWINGS

The following is a brief description of the drawings, in which:

FIG. 1A is a side elevational view of the apparatus of FIG. 1;

FIG. 5 is a front view of the gel tube rack in one embodiment of FIG. 3;

FIG. 6 is a side view of the gel tube rack of FIG. 5;

FIG. 7 is a top view of the gel tube rack of FIG. 5;

FIG. 9 is an end view of the gel slabs monitored in the supporting tray;

FIG. 10 is a schematic side view showing the gel being unloaded onto the edge of a gel slab;

FIG. 11 is an end view showing the bead of unload gel on the edge of the gel slab;

FIG. 15 is a side view in cross-section of an unloading device in a second embodiment of the invention.

DETAILED DESCRIPTION OF THE INVENTION

Figure 1:
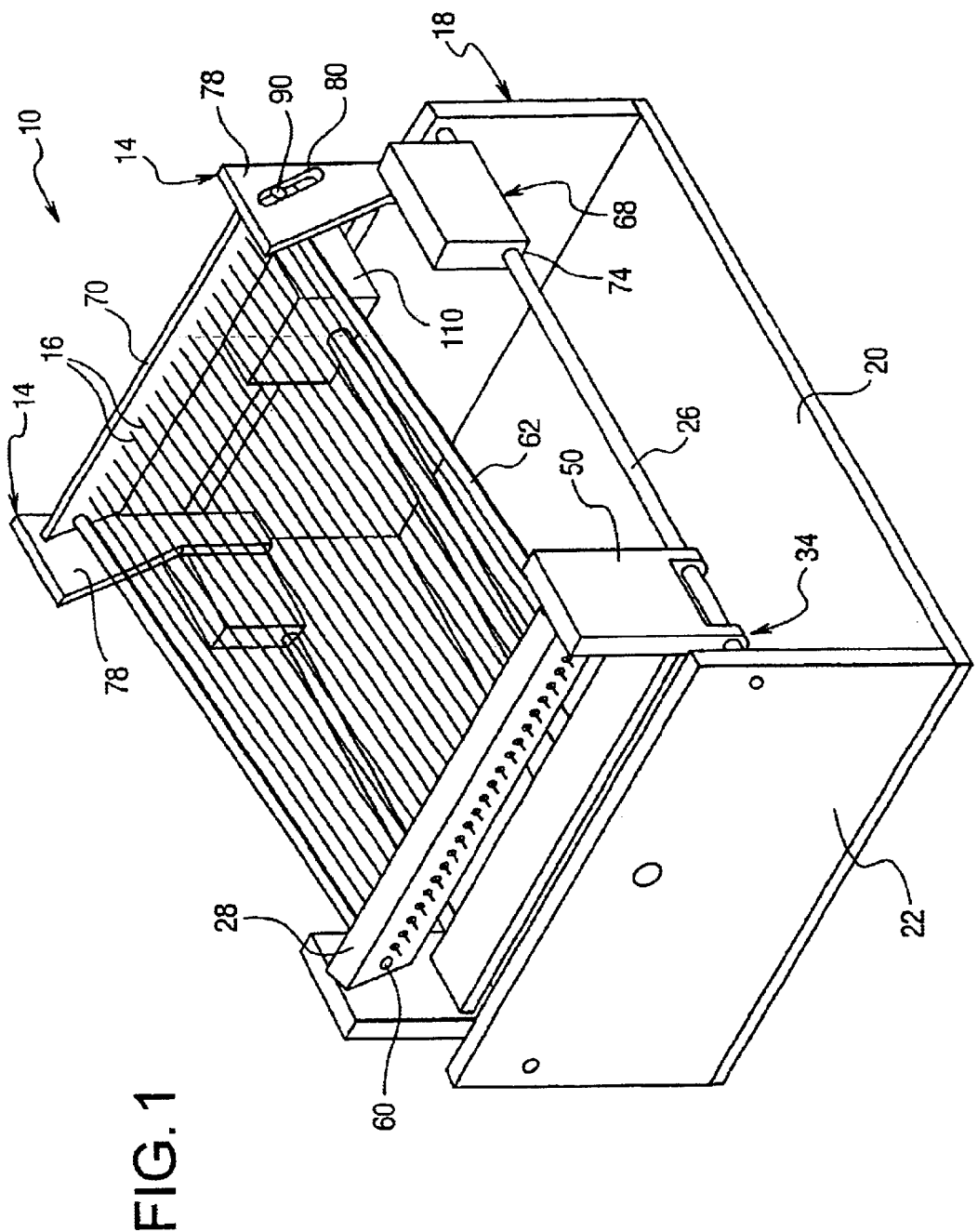
FIG. 1 is a perspective view of the unloading apparatus of the invention.

The present invention is directed to a method and apparatus for unloading and dispensing a substance from a tube. In particular, the invention is directed to a method and apparatus for unloading a substance from a tube in a controlled and uniform manner. The method and apparatus of the invention are primarily directed to transferring an isoelectric focusing gel from a gel tube onto the edge of a gel slab in a two dimensional separation process. A protein sample is subjected to a first dimensional electrophoresis separation as known in the art. The electrophoresis first dimension separation utilizes a cylindrical tube that is typically made of glass and has an internal diameter of about 0.5 mm to about 2 mm and a length of about 30 cm. The tube is filled with an isoelectric focusing gel, such as an acrylamide gel. The protein sample is applied to one end of the tube while each end of the tube is in contact with a buffer solution to define a pH gradient along the length of the tube. An electric potential is applied to each end of the tube where by the proteins migrate through gel. The gel must then be removed from the tube and placed on the end of the gel slab. It is essential for consistent results that the gel be transferred intact with minimal distortion of the gel body.

The apparatus of the invention is constructed to unload a gel from a tube onto a surface, and particularly a gel slab, without breaking the gel. The apparatus unloads the gel from the tube at a controlled rate while moving the end of the tube across the surface at a rate complementing the discharge rate so that the gel is unloaded in a controlled manner. It is particularly desirable to unload an isoelectric gel body from the gel tubes in a uniform manner to avoid elongation or compression in portions of the gel body. In embodiments of the invention, the apparatus is able to unload the gel with uniform elongation or compression as desired.

The apparatus of the invention is particularly constructed to remove an isoelectric focusing gel from the tube directly onto the edge of the gel slab for further separation of the proteins. Since the different proteins are spaced along the length of the gel, it is necessary to remove the gel without breaking the gel. The apparatus unloads the gel from the tube without distortion or twisting. Although the invention is primarily concerned with unloading gels, it will be understood that the apparatus and method are suitable for unloading a number of substances. For example, the apparatus and method can be used to unload capillary electrophoresis gels, ringing gels, DNA containing gels, paste-like, rubber-like or viscous creams. The apparatus can also be used to clean and remove gel residues from tubes after the bulk of the gel is transferred to a gel slab.

Referring to the drawings, the unloading apparatus 10 of the invention includes a first support assembly 12, a second support assembly 14, and a plurality of plunger rods 16.

First support assembly 12 is mounted on a base 18 as shown in FIGS. 1 and 1A. Base 18 includes a bottom rail 20, a pair of front posts 22 and two rear posts 24. A guide rail 26 extends from each front post 22 to the respective rear post 24. Preferably, two parallel guide rails 26 are provided on each side of base 18.

Figure 2:
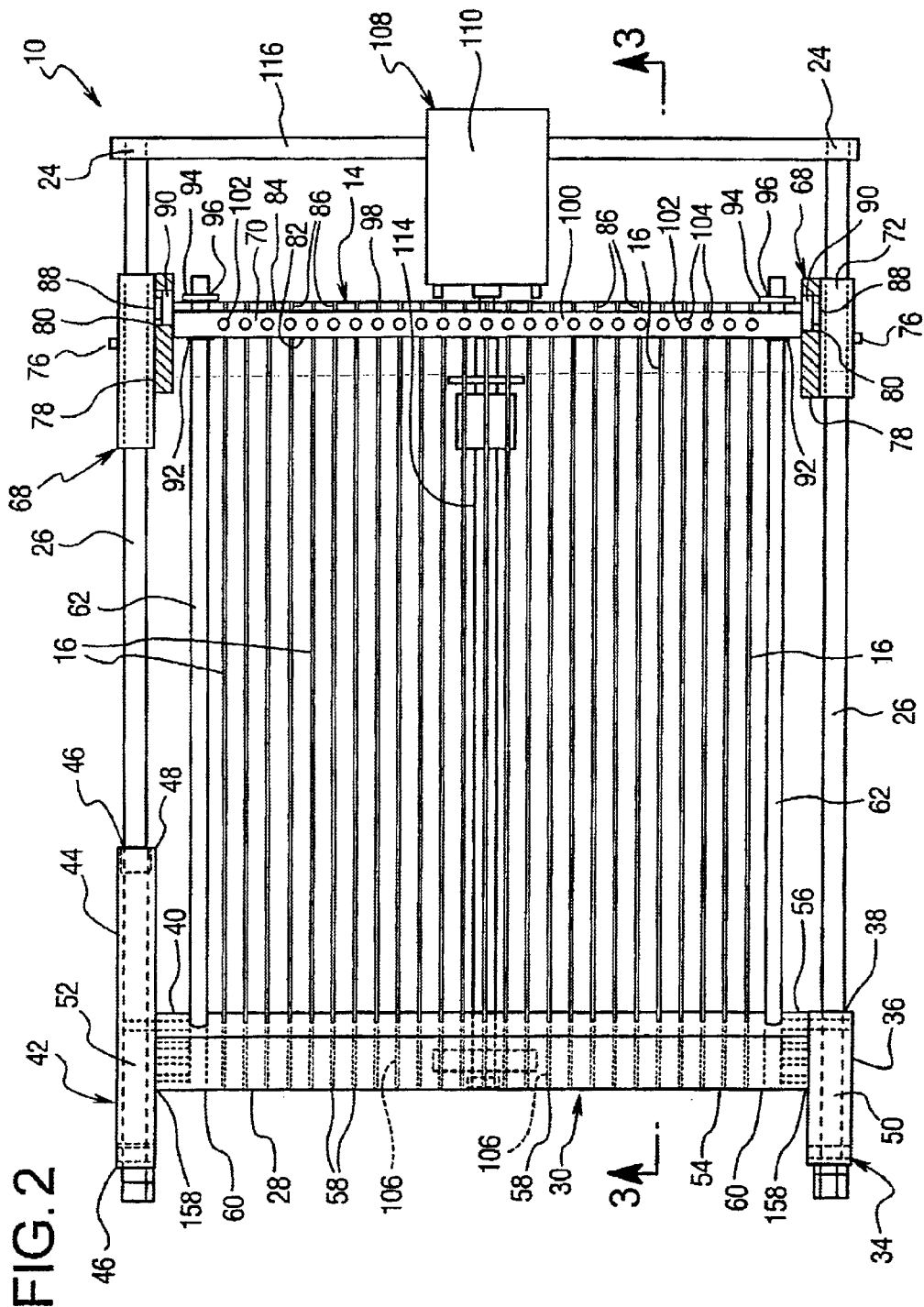
FIG. 2 is a top view of the apparatus of FIG. 1.
Figure 3:
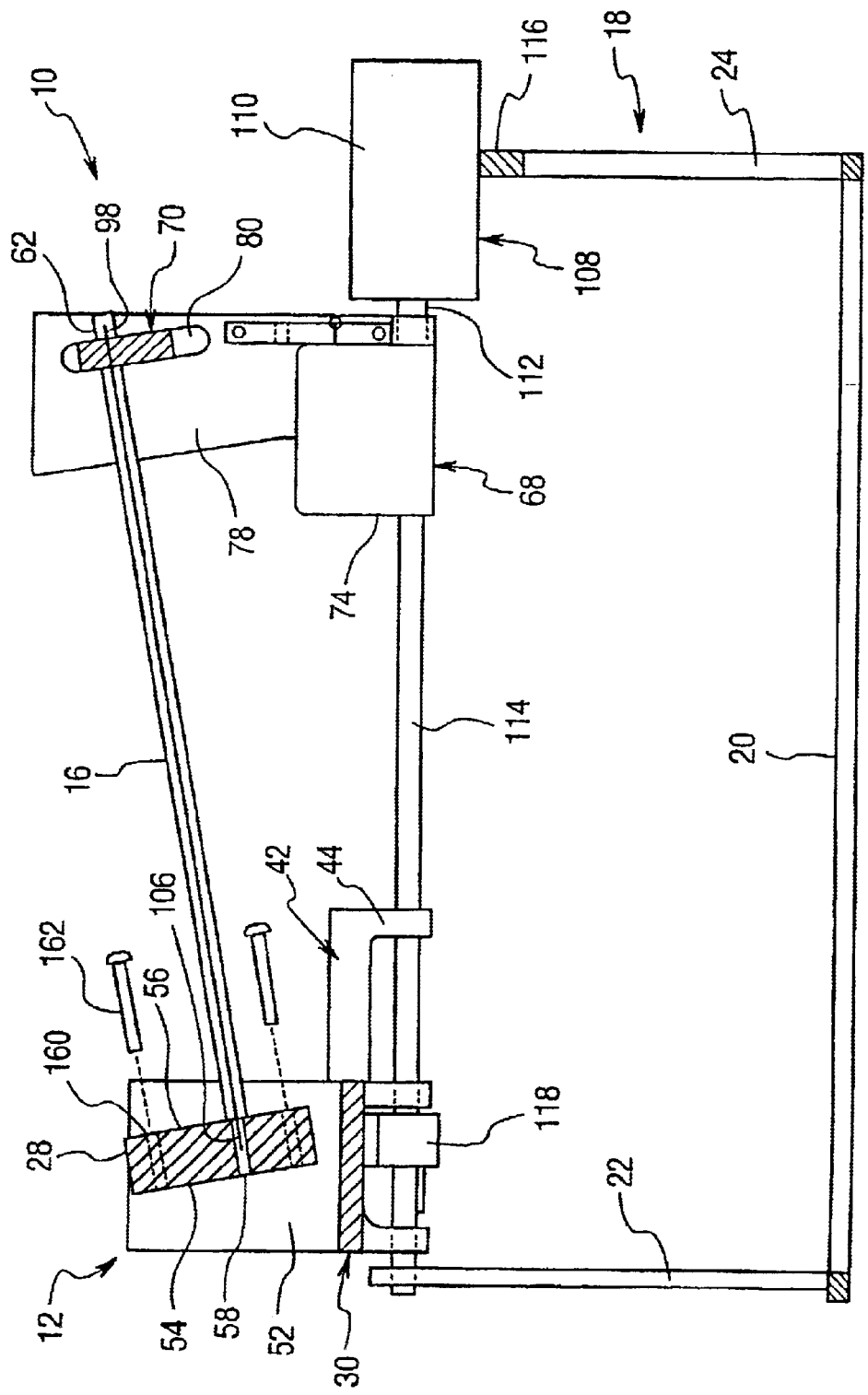
FIG. 3 is a cross-sectional side view of the apparatus taken along line 3—3 of FIG. 2.
Figure 4:
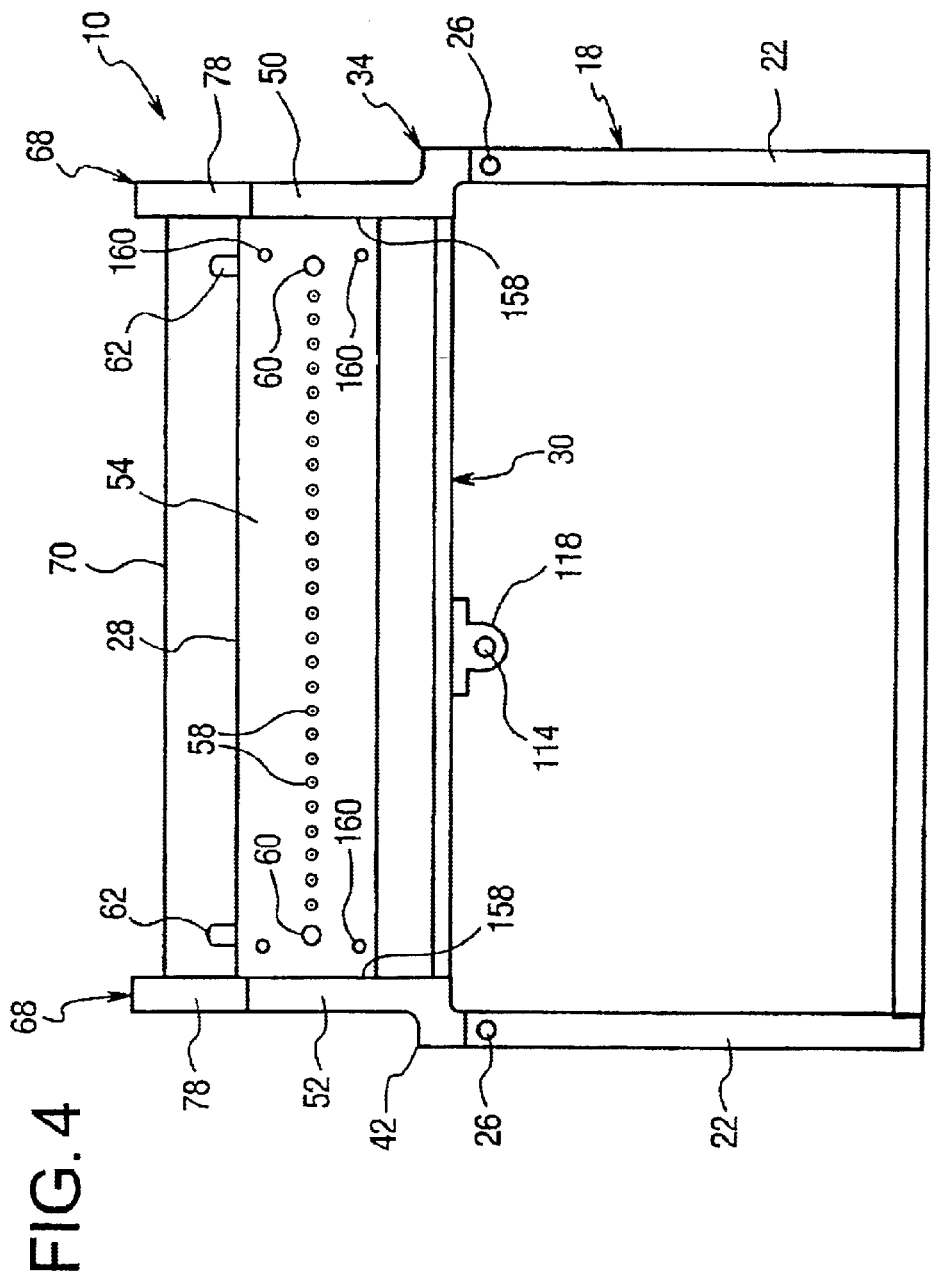
FIG. 4 is an end view of the rack in one embodiment of the invention.

First support assembly 12 includes a mounting plate 28 and a carriage 30. Carriage 30 has a longitudinal dimension corresponding to the width of base 18. A first end 32 of carriage 30 is connected to a bracket 34. Bracket 34 has two downwardly extending legs 36 with axially aligned bores 38. Bores 38 are dimensioned to complement guide rail 26 so that bracket 34 is able to slide on rail 26. Preferably, guide rail 26 is a substantially cylindrical shaped rod. Although rail 26 can be any suitable shapes. A second end 40 of carriage 30 includes a second bracket 42. Bracket 42 includes a pair of legs 44 with axially aligned bores 46 in a manner similar to the first bracket 34. Bracket 42 as shown in FIGS. 1 and 2 has a length greater than the first bracket 34. Second bracket 42 includes an end 48 forming a stop member as discussed hereinafter in greater detail. Brackets 34 and 42 are slidably mounted on a respective guide rail 26 as shown in FIG. 2 for sliding movement along the length of guide rails 26.

Bracket 34 and bracket 42 each include an end wall 50 and 52, respectively, extending in a generally upright direction. End walls 50 and 52 are united in a plane substantially parallel to the longitudinal dimension of guide rails 26. Mounting plate 28 is a substantially rectangular shaped plate having opposite ends coupled to a respective end wall 50 and 52 by screws 53 as shown in FIG. 1. Mounting plate 28 has a front face 54 and a rear face 56. A plurality of spaced apart openings 58 extend between front face 54 and rear face 56 as shown in FIG. 2. Openings 58 are uniformly spaced apart and aligned in a for extending between bracket 34 and bracket 42.

As shown in FIGS. 1 and 2, each end of mounting plate 28 includes a bore 60 extending between front face 54 and rear face 56. A rigid guide rod 62 is fitted into bores 60 to extend outwardly from rear face 56. In preferred embodiments, each guide rod 62 is fixed to mounting plate 28 and is substantially immovable with respect to mounting plate 28 and carriage 30. Each guide rod 62 extends from rear face 54 along an axis substantially parallel to the axis of openings 58 in mounting plate 28. Guide rod 62 can be press fitted into hoses 60 or secured in place by a screw or other fastener.

Second support assembly 14 includes a bracket 68 coupled to each guide rail 26 and a support bar 70. Each bracket 68 includes a leg 72 having a bore 74 complementing the dimension of guide rail 26. Guide rail 26 extends through each bore 74 for supporting brackets 68. The position of each bracket 68 can be adjusted along the length of guide rail 26. In preferred embodiments, brackets 68 include a coupling member such as a set screw 76 for fixing the position of bracket 68 on the respect guide rail 26.

Brackets 68 each include an upstanding end wall 78 extending upwardly from the direction. In the embodiment illustrated, slot 80, of guide rail 26 to extend. An elongated slot 80 is provided in each end wall 78 as shown in FIG. 1. Slot 80 has a longitudinal dimension extending in a generally vertical direction. In the embodiment illustrated slot 80 is oriented at an angle with respect to guide rail 26 to extend at an incline toward first support 12. In further embodiments as discussed thereinafter in greater detail shot 80 can be accented perpendicular to guide rail 26 or slightly inclined away from first support 12.

Support bar 70 extends between brackets 68 and includes a front face 82 and a rear face 84. A plurality of spaced apart openings 86 extend between front face 82 and rear face 84. Each end of support bar 70 includes a pinion 88 and a bearing 90. Bearing 90 is preferably a roller bearing that is dimensioned to fit and slide within slot 80 as shown in FIG. 2. Each end of support bar 70 also includes a bore 92 extending between front face 82 and rear face 84. In preferred embodiments, a bushing 94 having an axial passage 96 is fitted within each bore 92. Axial passage 96 of each bushing 94 is dimensioned to receive a respective guide rod 62. Guide rods 62 are dimensioned to slide through axial passage 96 of each bushing 94.

As shown in FIG. 2, a plurality of plunger rods 16 have a first end 98 received in a respective opening 86 of support bar 70. In the embodiment illustrated, support bar 70 has a top face 100 having a threaded bore extending into the axial passage of each opening 86. A set screw 102 is threaded into the bores to couple the first end 98 of each plunger rod 16 to support bar 70. Plunger rods 16 include a second end 106 received in a corresponding opening 58 of mounting plate 28. The location of a second end 106 of plunger rods 16 can be individually adjusted in opening 58 of mounting plate 28 by loosening screws 102 and adjusting the position of each plunger rod 16 in support of bar 70. The position of the adjusting the position of second support 14 on rails 26.

In the illustrated embodiment, brackets 68 are fixed to guide rails 26 during the use of the apparatus. The linear movement of support bar 70 and plunger rod 16 in the direction of guide rails 26 is limited by the incline of slot 80 with respect to guide rail 26. Carriage 30 and mounting plate 28 are slidable along guide rails 26 from an extended position shown in FIG. 1 toward to a retracted position second support assembly 14. The angle of mounting plate 28 and guide rods 62 remain constant with respect to guide rail 26 as carriage 30 slides along guide rail 26.

A drive assembly 108 is provided for sliding carriage 30 and mounting plate 28 along guide rails 26 at a constant speed. The illustrated embodiment drive assembly 108 includes a motor 110 operatively connected to a first end 112 of a threaded rod 114. Threaded rod 114 extends substantially parallel to guide rails 26 the embodiment illustrated, motor 110 is mounted on a cross support 116 extending between rear posts 24. A coupling 118 is connected to carriage 30 as shown in FIG. 1. Coupling 118 includes an internally threaded bore for coupling with a second end 120 of threaded rod 114. Motor 110 is energized to rotate threaded rod about its axis and move coupling 118 and carriage 30 along the axis of threaded rod 112. In a preferred embodiment, motor 110 is a reversible motor to rotate threaded rod 114 in different directions to selectively move carriage 30 toward or away from second support 14 depending on the direction of rotation of threaded rod 114.

In the illustrated embodiment, motor 110 is mounted adjacent second support at the rear of assembly 10. In further embodiments, motor 100 can be mounted toward the front end of base 18 with threaded rod 114 extending toward the rear end of base 18. Alternative drive assemblies can also be used, such, for example, a chain or gear drive.

Apparatus 10 is used in conjunction with isoelectric focusing gel tubes 122. Gel tubes 122, as shown in FIG. 5, have a substantially cylindrical shape with an axial passage 124, a first open end 126 and a second open end 128. Gel tubes 122 are mounted in a tube support members, such as a rack 130 as shown in FIG. 5. In the illustrated embodiments, gel tubes 122 have a cylindrical shape. In further embodiments, gel tubes 122 can have a non-circular cross-section such as an oval, square or rectangular shape. As used herein, the term "tube" is intended to refer to an elongated hollow body and is not limited to cylindrical shaped tubes.

Rack 130 is a support suitable for use in an electrophoresis tank during a first dimension electrophoresis separation process as known in the art. In one embodiment of the invention, rack 130 includes side walls 132 and a lower brace 134 extending between side walls 132. A plurality of spaced apart openings 136 dimensioned to receive gel tubes 122 are provided in lower brace 134. A trough assembly 128 is coupled to the top end of side walls 132 by screws 140 or other suitable fasteners. Trough 138 includes side walls 142 and a bottom wall 144. Bottom wall 144 includes a plurality of spaced apart openings 146 axially aligned with openings 136 and lower brace 134. An upper brace 148 extends between side walls 132 directly below bottom wall 144 of trough 138. Upper brace 148 also includes a plurality of spaced apart openings 150 aligned with openings 146 and 136. Side walls 142 and bottom wall 144 of trough 138 define a chamber 152 for containing a buffer solution as known in the art of first dimension electrophoresis separation.

Figure 7A:
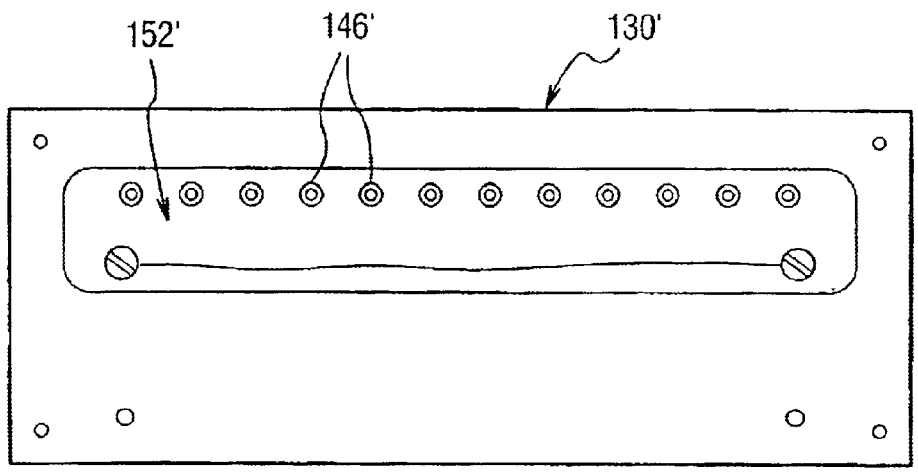
FIG. 7A is a top view of a gel tube rack in another embodiment.
Figure 7B:
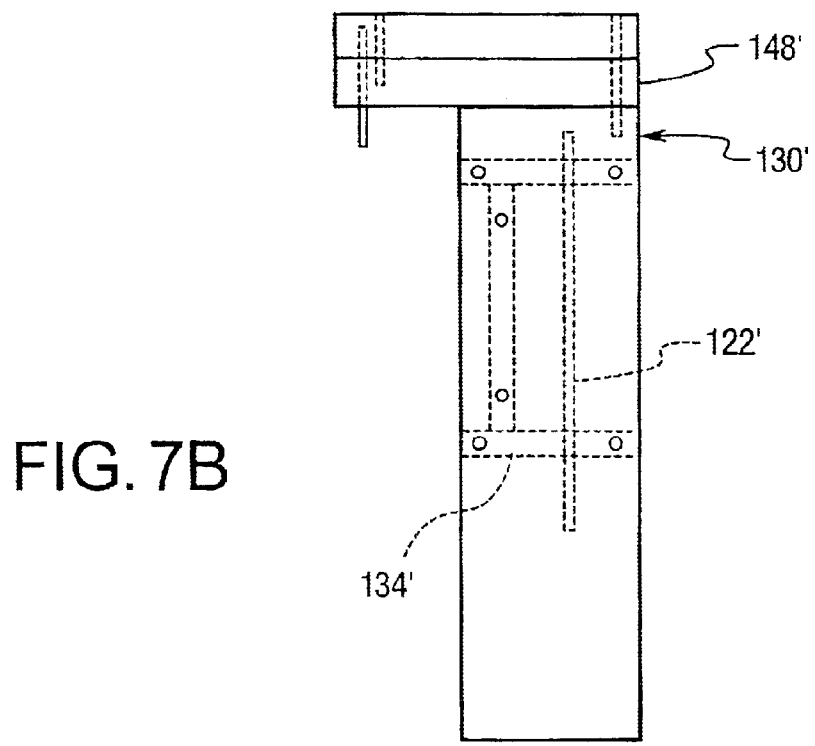
FIG. 7B is a side view of the rack of FIG. 7A.

In the illustrated embodiment, rack 130 supports two rows of gel tubes 122. The rack 130 shown in FIGS. 5–7 is an example of a suitable rack for supporting gel tubes 122, although it will be understood that other structures can be used. In one embodiment, a gel tube rack 130' as shown in FIGS. 7A and 7B includes a single row of gel tubes 122'. Rack 130' is similar to rack 130 and is coupled to unloading apparatus 10 in a similar manner with plunger rods 16 aligned with gel tubes 122'.

Referring to FIG. 5, trough 138 includes a top face 154. Top face 154 includes two internally threaded bores 156 adjacent each side edge 158. As shown in FIG. 1, mounting plate 28 includes complementing holes 160 aligned with threaded bores 156 of top face 154. Screws 162 extend through holes 160 in mounting plate 28 and are threaded into bores 156 of top face 154 to couple rack 130 to mounting plate 28. Threaded bores 156 in top face 154 are oriented with respect to holes 160 in mounting plate 28 to align openings 58 of mounting plate 28 and respective plunger rod 16 with a row of gel tubes 122. It will be appreciated that openings 58 in mounting plate 28 and plunger rod 16 are spaced apart a distance corresponding to the spacing of gel tubes 122 in rack 130. Preferably, the number of gel tubes 122 in rack 130 correspond to the number of plunger rods 16 in apparatus 10. In the embodiment shown in the drawings, a single row of plunger rods 16 are provided and aligned with one row of gel tubes 122 in rack 130. Preferably threaded bores 156 in top face 154 of rack 130 are positioned so that rack 130 can be inverted with respect to mounting plate 28 to align plunger rods 16 with a selected row of all tubes 122. In this manner, each row of gel tubes 122 can be unloaded by inverting rack 130 and reinstalling on mounting plate 28.

Figure 8:
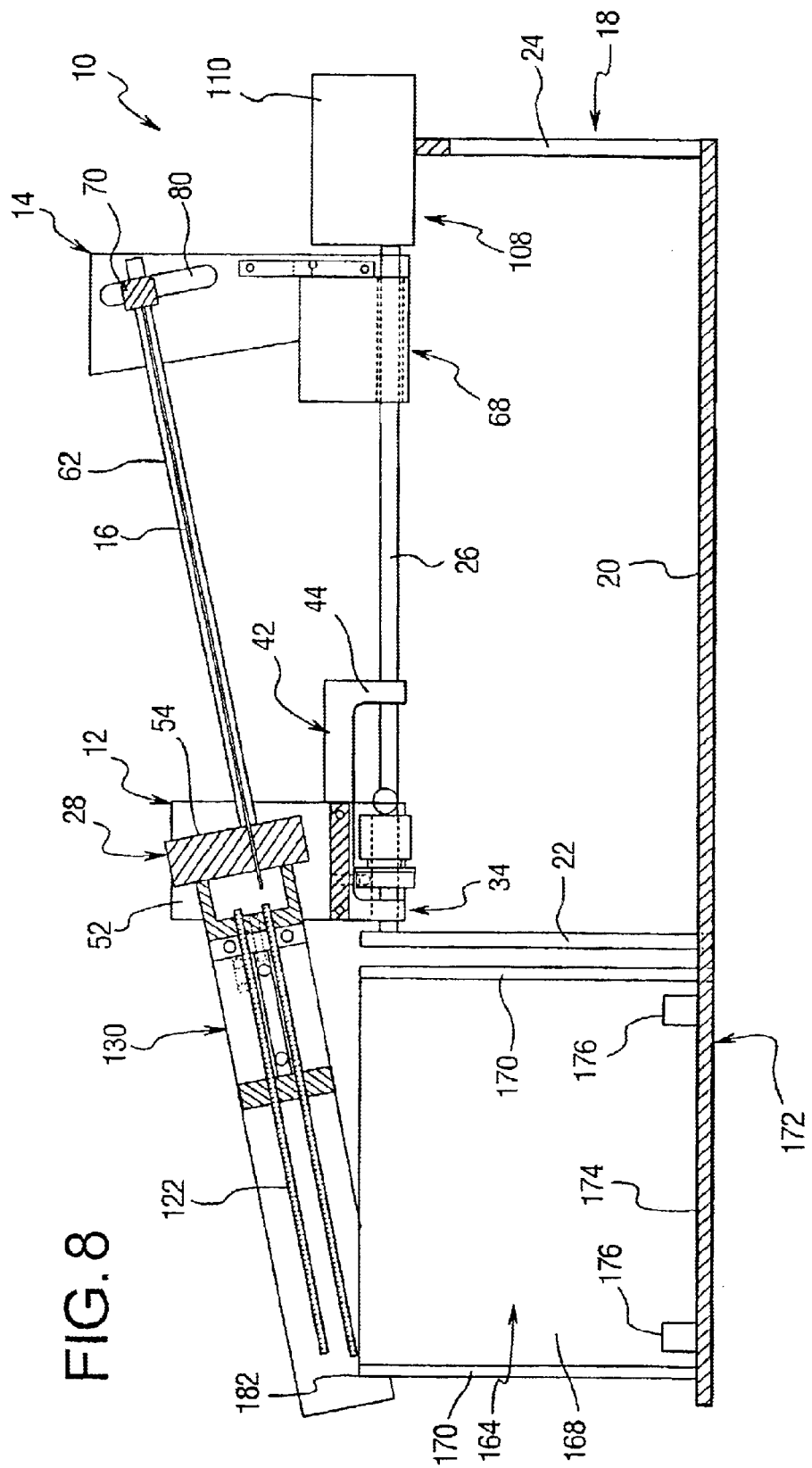
FIG. 8 is a side view of the assembly showing the gel slabs and gel tube rack coupled to the unloading apparatus.
Figure 13:
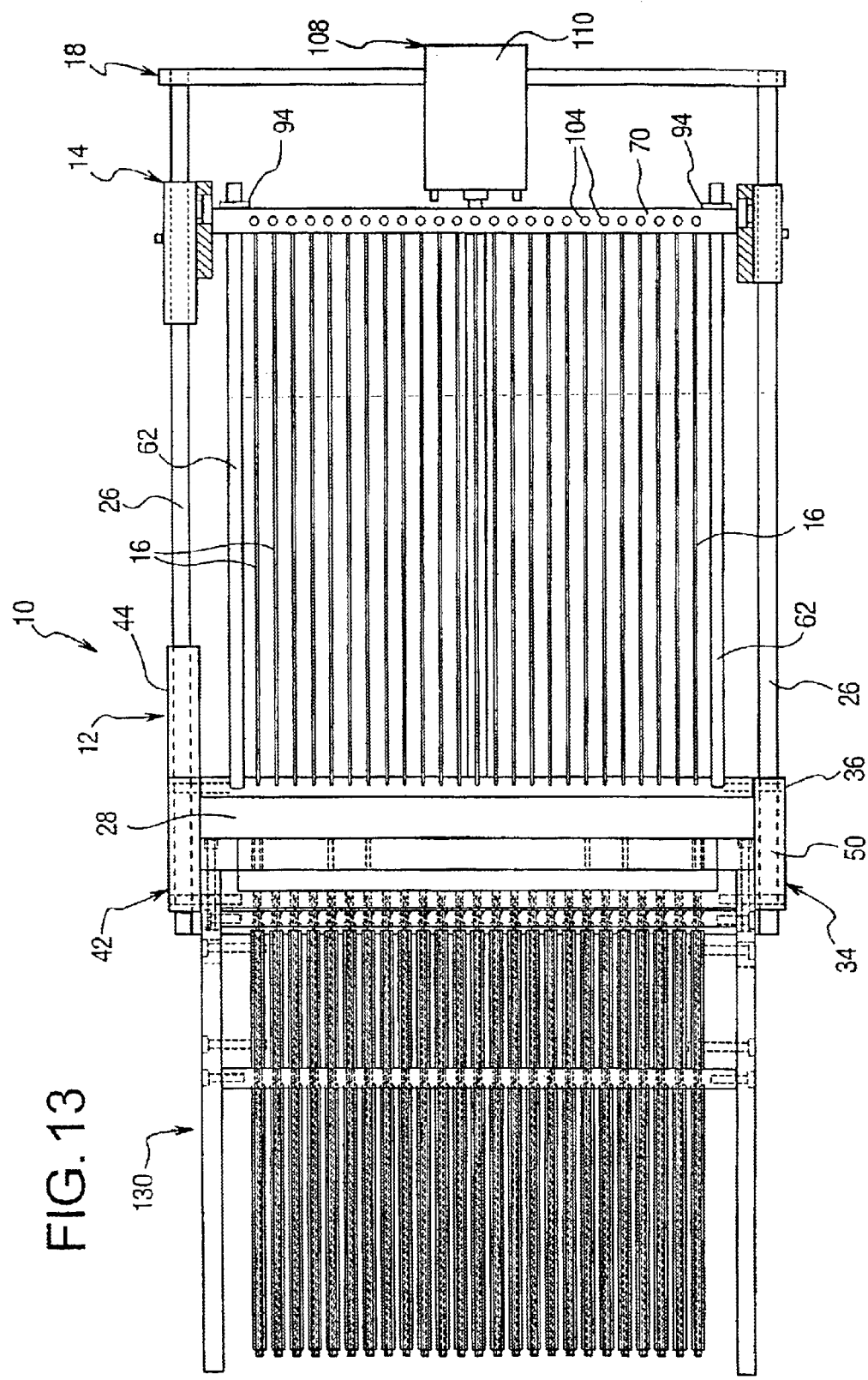
FIG. 13 is a top view of the assembly of FIG. 8.
Figure 14:
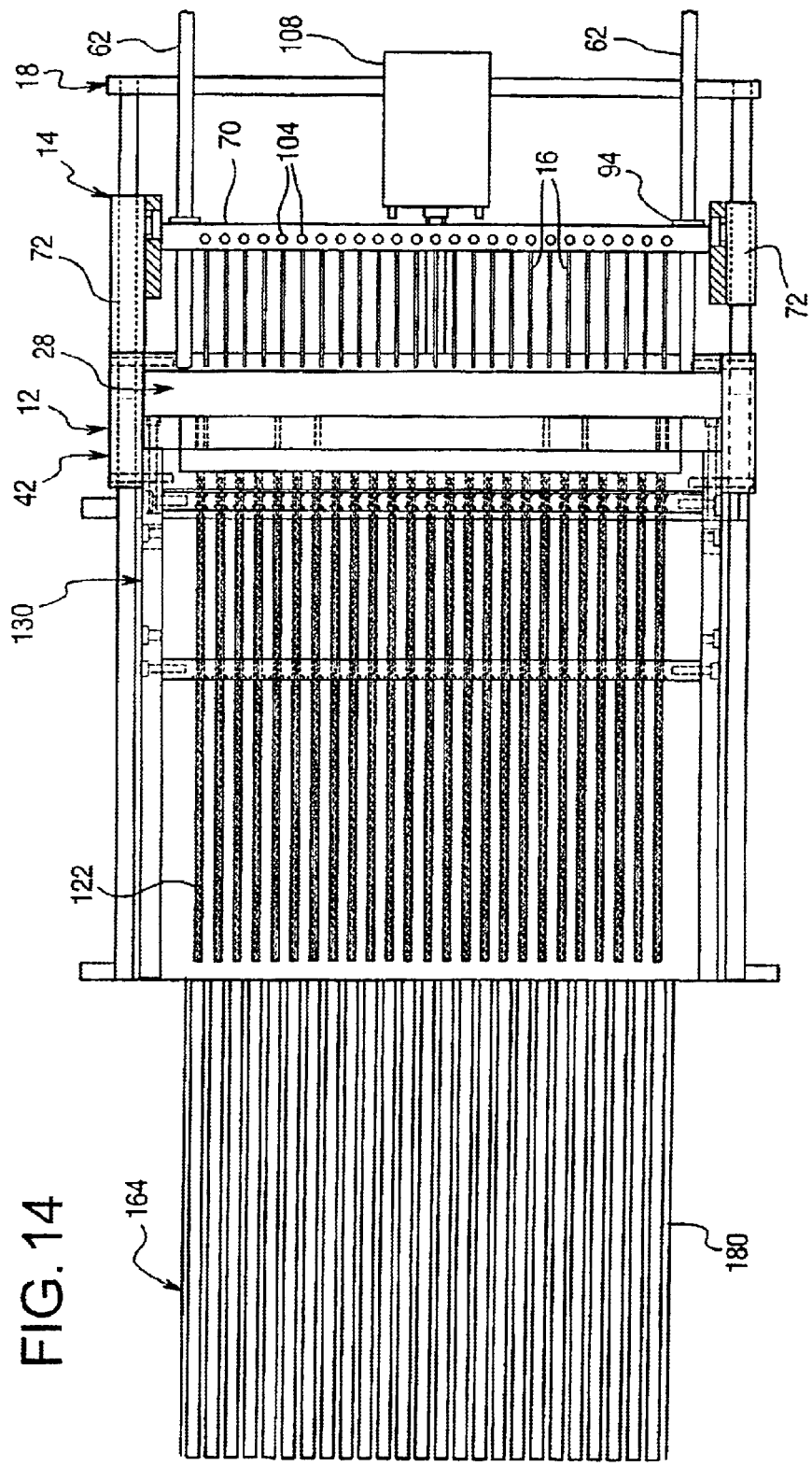
FIG. 14 is a top view of the assembly of FIG. 8 showing the position of the gel tubes after the gel is unloaded.

As discussed hereinafter in greater detail, apparatus 10 is primarily intended for use in transferring the isoelectric focusing gel from a respective gel tube 122 onto a gel slab 164 for conducting a second dimension separation as known in the art. Gel slabs 164 in preferred embodiments of the invention include a layer of an electrophoresis focusing gel 166 sandwiched between two glass plates 168 as shown in FIG. 9. Typically, a spacer 170 in the form of a narrow glass strip is positioned adjacent each end of glass plates 168 as shown in FIG. 8 to provide uniform spacing of glass plates 108. Gel slabs 164 are supported in a tray 172 that is coupled to apparatus 10 adjacent front post 22. Tray 172 includes a bottom wall 174 and spaced apart ribs 176 extending substantially perpendicular from bottom wall 174 a sufficient distance to support gel slabs 164. Preferably, ribs 176 are spaced apart a distance corresponding to the thickness of gel slabs 164 to support gel slabs 164 in an upright fashion as shown in FIG. 9. Ribs 176 are dimensioned to position gel slabs 164 in a spaced apart relation corresponding to the spacing between gel tubes 122 of rack 130 as shown in FIGS. 13 and 14. Gel slabs 164 are oriented in an upright position parallel to gel tubes 122 and with a substantially horizontal upper edge 178.

Gel tubes 122 containing an isoelectric focusing gel 180 are fitted into rack 130 for use in a first dimension electrophoresis separation of a biological sample. After the electrophoresis separation is completed, rack 130 with gel tubes 122 still attached is coupled to mounting plate 28 by screws 162. As shown in FIG. 8, mounting plate 28 substantially perpendicular to the longitudinal axis of gel tubes 122 in rack 130, and plunger rods 16 are coaxially aligned with a respective gel tube 122. Gel slabs 164 are positioned in tray 172 and aligned with a corresponding gel tube 122. As shown in FIG. 13, first end 126 of gel tubes 122 are aligned with openings 58 in mounting plate 28 and a respective plunger rod 16. Second end 128 of gel tubes 122 are positioned on or slightly above upper edge 178 of gel slab 164 adjacent a first end 182. As shown in FIG. 8, mounting plate 28 is oriented at an angle with respect to guide rails 26 and upper surface 178 of gel slabs 164. In embodiments of the invention, mounting plate 28 can include a coupling assembly such as an elongated slot and screw member for adjusting the angular position of mounting plate 28 with respect to upper edge 178 of gel slabs 164. Carriage 30 is moved to the extended position shown in FIG. 6 by actuating motor 110 to position second end 128 of gel tube 122 at first end 182 of gel slab 164. Second support assembly 14 is then adjusted on guide rails 26 until second end 106 of plunger rods 16 are positioned at first end 126 of gel tubes 122.

As shown in FIG. 10, plunger rods 16 have an outer dimension corresponding substantially to the dimension of axial passage 124 of gel tubes 122. In practice, plunger rods 16 have a diameter slightly less than the internal diameter of axial passage 124 to be able to slide through axial passage 124 without interference. It has been found that plunger rods 16 are able to express gel 180 from gel tubes 122 onto gel slabs 164. However, the variations in texture of gel 180 in gel tubes 122 can result in pieces of the gel adhering to the inner surface of tube 122 being broken away and separated from the gel body as the gel is unloaded from the gel tube. In a preferred embodiment of the invention, a plunger member 184 is placed in the second end 126 of gel tubes 122 between gel 180 and second end 106 of plunger rods 16 as shown in FIG. 10. Plunger member 184 is preferably made of a resilient material having a diameter slightly greater than the internal diameter of axial passage 124 of gel tube 122 to prevent pieces of the gel from adhering to the surface of the tube. In preferred embodiments, plunger member 184 is a ball shaped member made of a silicone rubber. The silicone rubber ball has an outer dimension that is able to contact the inner surface of axial passage 124 and is able to pass through axial passage by the force applied by plunger rod 16. Plunger member 184 in combination with plunger rods 16 are able to consistently unload the gel as a continuous body with little or no tearing, breaking or distortion of the gel.

Figure 12:
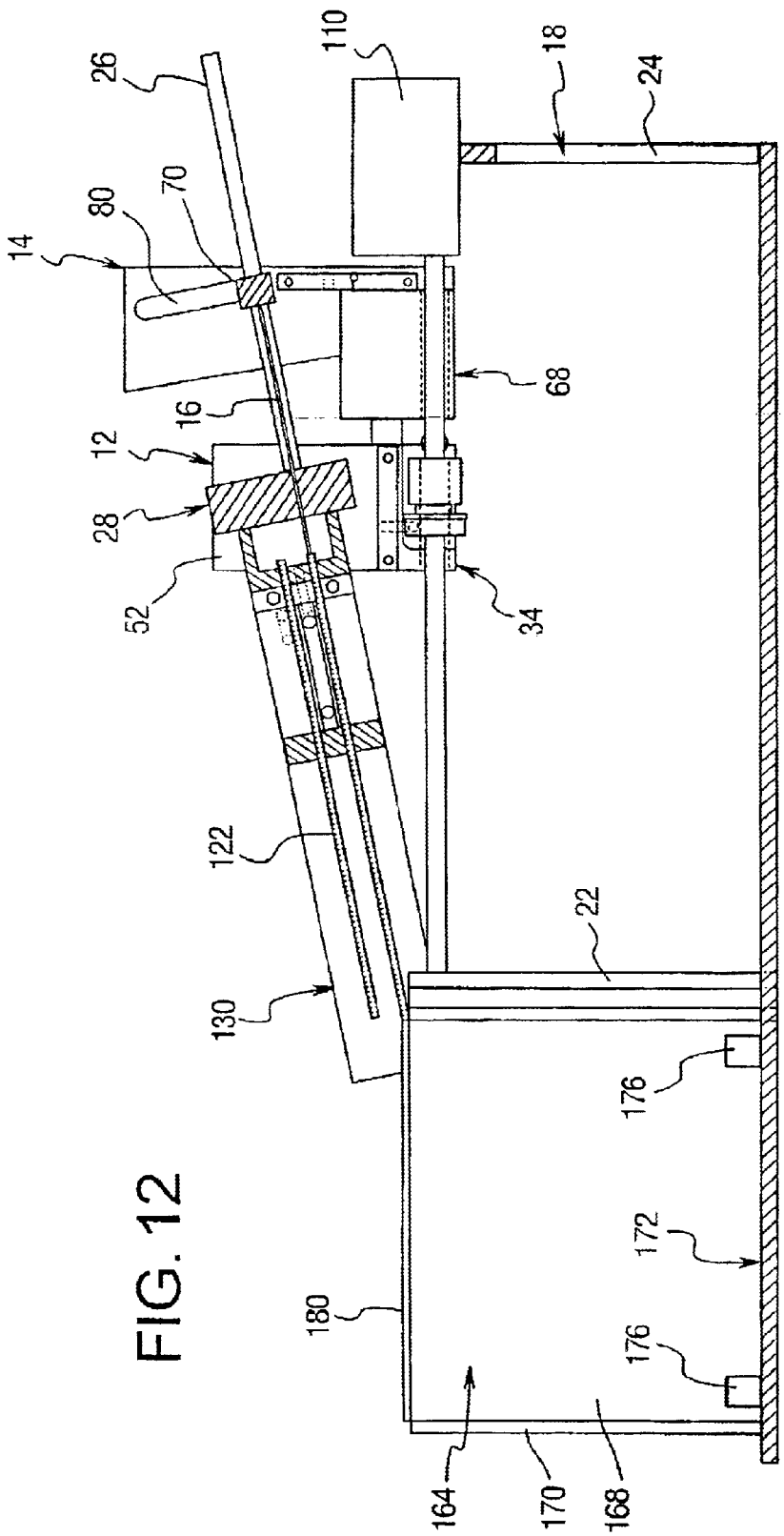
FIG. 12 is side view of the assembly of FIG. 8 showing the position of the gel tubes after the gel is unloaded.

Rack 130 is coupled to mounting plate 28 and gel tubes 122 are aligned with a respective gel slab 164. Motor 110 is then actuated to rotate threaded rod 112. Rotation of threaded rod 112 pulls carriage 30 and mounting plate 28 at a constant speed toward second support assembly 14. First end 98 of plunger rods 16 are coupled to support bar 70 so that gel tubes 122 slide onto plunger rods 16 and express and unload gel 80 from gel tubes 122 onto upper edge 178 of gel slabs 164. Motor 110 is operated at a speed to unload gel 80 from gel tubes 122 at a controlled and uniform rate. As shown in FIG. 12, guide rods 62 slide through bore 92 of support bar 70 to maintain plunger rods 16 in axial alignment with gel tubes 122 and to maintain gel tubes 122 at a constant angle with respect to gel slabs throughout the unloading process. Motor 110 is operated until carriage 30 travels a distance sufficient to unload gel 180 onto gel slabs 164 as shown in FIGS. 10 and 11. At that time, gel slabs 164 are removed from tray 172 and transferred to a suitable second dimension electrophoresis separation apparatus.

As shown in FIGS. 8 and 12, the angle of mounting plate and guide rods 62 with respect to guide rails 26 causes support bar 70 and bearings 90 to slide within slot 80 of end walls 78 of brackets 68. In the embodiment illustrated, slot 80 is oriented at an incline so that support bar 70 moves away from gel slabs 164 as carriage 30 is moved toward second support assembly 14. It will be understood that the actual angle of slot 80 will determine the amount of movement of support bar 70 during movement of carriage 30. In this embodiment, plunger rods 16 are moved away from gel slabs 164, as carriage and gel tubes 122 are moved toward second support 14 so that the end of gel tubes 122 slide along the top edge of gel slabs 164 at the same or a slightly faster rate than the rate than the rate that the gel body 180 is being unloaded. In preferred embodiments, the ratio of the rate of unloading the gel to the rate of the movement of the gel tubes across the gel slabs is about 1 to 1. This coordinated movement of plunger rods 16 and gel tubes 122 result in gel 80 being slightly stretched or elongated as it is unloaded from gel tube 122. In further embodiments, slot 80 can be oriented substantially perpendicular to guide rails 26 so that gel 80 in gel tube 122 is unloaded onto gel slabs 164 with substantially no elongation or compaction during unloading. In still further embodiments, slot 80 can be oriented to move support bar 70 toward gel slabs 164 during movement of carriage 30 to compress gel 180 as it is unloaded from the gel tubes 122.

A second embodiment of the invention as shown in FIG. 15 is a manually operated unloading device 200. Unloading device 200 is a hand held device having a housing 202 with a generally cylindrical shape with a first end 204 and a second end 206. First end 204 has a flange 208 extending radially outward a distance sufficient for an operator to grip device 200.

Housing 202 has an axial passage 210 extending between first end 204 and second end 206. Axial passage 210 has a first cylindrical section 212 extending from second end 206 and is dimensioned to receive a gel tube 214. A second cylindrical section 216 extends from first end 204 and joins first section 212 to define a stepped portion 218. A plunger rod 220 has a first end 222 extending through axial passage 210 from first end 204. A second end 224 of plunger rod 220 includes an actuator member 226.

In preferred embodiments, plunger rod 220 is a cylindrical shaped member made from metal or other sufficiently rigid material to expel and unload the gel from gel tube 214. Typically, plunger rod 220 has an outer dimension to slide easily through gel tube 214 and apply a uniform pressure on plunger member 220.

Gel tube 214 has a first open end 217, second open end 219, and an axial bore 221 containing a gel. As shown in FIG. 15, gel tube 214 has open end 217 fitted into first section 212 so that the end seats against stepped portion 218 and holds gel tube 214 in housing 202. In preferred embodiments, gel tube 214 is coupled to housing 202 by a friction fit. A resilient plunger member in the form of a spherical rubber ball 228 is placed in the end of gel tube 214 as in the previous embodiments. Plunger rod 220 is actuated by manually pressing actuator member 226 while the operator holds housing 202. The open end 219 of gel tube 214 is moved across the end of a gel slab 230 while discharging an IEF gel material 232 onto gel slab 230. As in the previous embodiment, ball 228 in combination with plunger rod 220 effectively discharges gel 232 without distortion. Ball 228 applies a substantially uniform pressure across the diameter of gel 232 in gel tube 214 to unload the gel as a continuous line.

In the embodiment shown, gel tube 214 is dimensioned to fit securely in housing 202. In alternative embodiments, a rubber-like grommet or gasket can be provided in axial passage 210 to secure gel tube 214 in place.

Unloading device 200 is used in a method for unloading gels from a gel tube in a singular fashion onto a gel slab. In further embodiments, housing 202 can include a plurality of parallel axial passages for supporting a plurality of gel tubes. In the method of the invention, gel tube 214 is inserted into axial passage 210 and a plunger member 228 is placed in axial passage 210 and aligned with the axial bore 221 of gel tube 214. Plunger rod 220 is then inserted into axial passage 210 of housing 202 and aligned with plunger member 228 and axial bore 221 of gel tube 214. Plunger rod 220 is then actuated to push plunger member 228 through gel tube 214 to unload the gel.

In the illustrated embodiments of FIGS. 5–12, rack 130 includes two parallel rows of gel tubes 122. In further embodiments, gel tubes 122 can be oriented in various other arrangements. For example, a gel tube rack can be formed with recesses for supporting a plurality of gel tubes in a non-linear pattern, such as circular, square or rectangular pattern.

In another embodiment of the invention, a gel tube rack is provided with two parallel rows with recesses for supporting gel tubes where the rows are staggered with respect to each other. In this embodiment, the two rows of gel tubes are staggered so that both rows of gel tubes can be aligned with a gel slab and unloaded simultaneously. Preferably, the gel slabs are supported in a tray where the upper edges of every other gel slab is staggered to complement the staggering of the gel tubes in the rack. The unloading device includes a complementing number of plunger rods aligned with each gel tube. In this manner, two rows of gel tubes are unloaded simultaneously onto staggered gel slabs. Staggering the gel slabs provides an arrangement to separate the unloaded gels and reduce the possibility of the adjacent gels contacting each other.

While various embodiments of the invention have been illustrated, it will be understood by those skilled in the art that additions and modifications can be made without departing from the scope of the invention as set forth in the appended claims.

What is claimed is:

1. An apparatus for unloading a substance from a tube, said apparatus comprising:
   a first support for supporting a plurality of tubes, each of said tubes having an axial passage, a first open end and a second open end, said first end of said tube being coupled to said first support;
   a second support spaced from said first support;
   a plurality of plungers having a first end coupled to said second support and a second end axially aligned with an axial passage of a respective tube; and
   a drive assembly for moving said first support along a linear path toward said second support, whereby said tubes slide onto said respective plunger to unload said substance from said second end of said tubes.

2. The apparatus of claim 1, further comprising a base, wherein said first support is movable along said linear path with respect to said base and wherein said second support is substantially immovable with respect to said base.

3. The apparatus of claim 2, further comprising at least one guide rail extending between said first support and said second support, wherein said first support is movable along said guide rail.

4. The apparatus of claim 3, wherein said first support comprises a carriage operatively connected to said guide rail.

5. The apparatus of claim 4, wherein said carriage includes a bore receiving said guide rail, said carriage being slidable on said guide rail.

6. The apparatus of claim 2, wherein said drive assembly comprises:
   a threaded shaft oriented along said linear path, and
   a coupling member attached to said first support, said coupling member having a bore with internal threads coupled to said threaded shaft; and
   a motor coupled to said threaded shaft for rotating said shaft to move said first support along said linear path toward said second support.

7. The apparatus of claim 6, wherein said motor is a reversible direction motor.

8. The apparatus of claim 1, wherein said first support comprises a mounting plate having a first side, a second side and a plurality of spaced-apart openings extending between said first side an said second side, and where said second end of said plungers are received in a respective opening in said mounting plate.

9. The apparatus of claim 8, wherein said first support assembly further comprises:
   a rack for supporting said tubes, said rack having a top wall with a plurality of openings for receiving said first end of said tubes, said rack being coupled to said coupling member with said opening of said top wall of said rack aligned with a respective opening of said coupling member.

10. The apparatus of claim 1, wherein said plurality of tubes having an outer dimension complementing said axial passage of said tubes.

11. The apparatus of claim 1, further comprising a plunger member received in said first end of said plurality of tubes between said substance in said plurality of tubes and said second end of said plurality of plunger.

12. The apparatus of claim 11, wherein said plunger member is made of a flexible material and has an external dimension complementing said axial passage of said tubes.

13. The apparatus of claim 12, wherein said plunger member is a substantially spherical shaped member.

14. The apparatus of claim 12, wherein said plunger member is a silicone rubber ball.

15. The apparatus of claim 1, wherein said plurality of plungers are oriented at an incline with respect to said linear path.

16. The apparatus of claim 15, wherein said second support maintains said plurality of plungers at said incline through movement of said first support along said linear path.

17. The apparatus of claim 15, wherein said second support comprises:
   a support bar having a first end and a second end, said first end of said plurality of plungers being coupled to said support bar;
   a first bracket coupled to said first end of said support bar; and
   a second bracket coupled to said second end of said support bar.

18. The apparatus of claim 17, further comprising at least one guide member having a first end coupled to said first support and a second end coupled to said second support and extending substantially parallel to said plurality of plungers.

19. The apparatus of claim 18, wherein said first end of said at least one guide member is fixed to said first support and said second end of said guide member is slidably coupled to said support bar.

20. The apparatus of claim 19, wherein said guide member is a rod and said support bar includes an opening extending therethrough and having an internal dimension complementing said rod to allow said rod to slide through said opening.

21. The apparatus of claim 19, wherein said first and second brackets have an elongated slot and said ends of said support bar are received in said slot of a respective bracket, wherein said ends of said support bar slide within said slots as said first support moves along said linear path.

22. The apparatus of claim 21, further comprising a bearing member coupled to each end of said support bar, and said bearing members being received in a respective slot of said first and second brackets.

23. The apparatus of claim 18, wherein said at least one guide member comprises two spaced apart guide members.

24. An apparatus for unloading a substance from a tube onto a surface, said apparatus comprising:
   a first support having a first side and a second side with at least one aperture extending between said first side and said second side, and having a movable carriage;
   a tube support member for supporting at least one tube containing said substance, said tube support member being coupled to said first side of said first support so that said tube is aligned with said at least one aperture;
   a second support spaced from said first support;
   at least one plunger rod having a first end coupled to said second support and a second end received in said at least one aperture of said first support; and
   a drive assembly for moving said carriage, in a linear path toward said second support whereby said plunger rod passes through said tube to unload said substance onto a surface.

25. The apparatus,of claim 24, further comprising a base and at least one guide rail, wherein said carriage is slidably mounted on said at least one said guide rail and is movable along said linear path with respect to said base and wherein said second support is substantially immovably mounted with respect to said base.

26. The apparatus of claim 25, wherein said carriage includes a bore receiving said guide rail, whereby said carriage is slidable on said at least one guide member.

27. The apparatus of claim 24, wherein said drive assembly comprises:
   a threaded shaft oriented along said linear path;
   a coupling member attached to said carriage, said coupling member having a bore with internal threads coupled to said threaded shaft; and
   a motor coupled to said threaded shaft for rotating said shaft to move said carriage along said linear path toward said second support.

28. The apparatus of claim 24, wherein said first support member comprises a mounting plate and, at least one said aperture extending between said first side and said second side, and where said second end of said at least one plunger rod are received in a respective opening in said mounting plate.

29. The apparatus of claim 28, wherein said tube support member comprises:
   a rack for supporting said at least one tube, said rack having a top wall with at least one opening for receiving a first end of said at least one tube, said rack being coupled to said mounting plate with at least one opening of said top wall of said rack aligned with a respective opening of said mounting plate.

30. The apparatus of claim 24, further comprising a plunger member received in said first end of said at least one tube between said substances and said second end of at least one plunger rod.

31. The apparatus of claim 30, wherein said plunger member is a substantially spherical shaped member.

32. The apparatus of claim 30, wherein said plunger member is a silicone rubber ball, said plunger rods are oriented at an incline with respect to said linear path, and wherein said second support maintains at least one plunger rod at said incline throughout movement of said carriage along said linear path.

33. The apparatus of claim 32, wherein said second support comprises:
   a support bar having a first end and a second end, said first end of at least one plunger rod being fixed to said support bar;
   a first bracket coupled to said first end of said support bar; and
   a second bracket coupled to said second end of said support bar.

34. The apparatus of claim 33, further comprising a guide member having a first end coupled to said carriage and a second end coupled to said second support and extending substantially parallel to said plunger rods.

35. The apparatus of claim 34, wherein said first end of said guide member is fixed to said carriage and said second end of said guide member is slidably coupled to said support bar.

36. The apparatus of claim 35, wherein said guide member is a rod and said support bar includes an opening extending therethrough and having an internal dimension complementing said rod.

37. The apparatus of claim 35, wherein first and second brackets have an elongated slot and said ends of said support bar are received in said slot of a respective bracket wherein said ends of said support bar slide within said slots as said carriage moves along said linear path.

38. The apparatus of claim 37, further comprising a bearing member coupled to each end of said support bar, and said bearing members being received in a respective slot of said brackets.

39. An apparatus for unloading an electrophoresis gel from an electrophoresis gel tube onto a gel slab, said apparatus comprising:
   a first support having a first side and a second side with a plurality of apertures extending through said first support between said first side and said second side and having a movable carriage;
   a gel tube member having a plurality of electrophoresis gel tubes containing said electrophoresis gel, said electrophoresis gel tube having a first end coupled to said gel tube support member and a second end spaced from said first support member, said gel tube support member being coupled to said first side of said first support so that said electrophoresis gel tubes are aligned with said plurality of apertures;
   a second support spaced from said first support;
   a plurality of plunger rods having a first end coupled to said second support and a second end received in said plurality of apertures of said first support;
   a plurality of vertically oriented gel slabs having their top edges aligned with plurality of electrophoresis gel tubes; and
   a drive assembly for moving said carriage toward said second support whereby plurality of plunger rods passes through said plurality of electrophoresis gel tubes to unload said electrophoresis gel onto said top edges of said plurality of vertically oriented gel slabs.

40. The apparatus of claim 39, further comprising a base and a guide rail coupled to said base, wherein a carriage is slidably mounted on said guide rail along a linear path with respect to said base and wherein said second support is immovable with respect to said base.

41. The apparatus of claim 40, wherein said drive assembly comprises:
   a threaded shaft oriented along said linear path, and
   a coupling member attached to said first support, said coupling member having a bore with internal threads coupled to said threaded shaft; and
   a motor coupled to said threaded shaft for rotating said shaft to move said carriage along said linear path toward said second support.

42. The apparatus of claim 39, wherein said first support member comprises a mounting plate having a first side, a second side and said plurality of apertures extending between said first side and said second side, and where said second end of said plunger rods are received in a respective opening in said first support member.

43. The apparatus of claim 42, wherein said gel tube support member comprises:
   a rack for supporting said plurality of electrophoresis gel tubes, said rack having a top wall with said plurality of openings for receiving said first end of said plurality of electrophoresis gel tubes, said rack being coupled to said mounting plate with said plurality of openings of said top wall of said rack aligned with said plurality of apertures in said mounting plate.

44. The apparatus of claim 39, further comprising a plunger member received in said first end of each of said plurality of electrophoresis gel tubes between said gel in each of said plurality of electrophoresis gel tubes and said second end of each of said plurality of plunger rods.

45. The apparatus of claim 44, wherein said plunger member is a substantially spherical shaped member made from a resilient cone rubber material.

46. The apparatus of claim 39, wherein said second support comprises:
   a support bar having a first end and a second end, said first ends of said plurality of plunger rods being fixed to said support bar;
   a first bracket coupled to said first end of said support bar; and
   a second bracket coupled to said second end of said support bar, said support bar being movable with respect to said first and second brackets upon movement of said carriage along said linear path to maintain said plurality of electrophoresis gel tubes at a substantially constant angle with respect to said plurality of vertically oriented gel slabs.

47. The apparatus of claim 46, further comprising two spaced apart guide members having a first end coupled to said carriage and a second end slidably coupled to said support bar and extending substantially parallel to said plunger rods.

48. The apparatus of claim 47, wherein said guide members comprises a rod, and said support bar includes two spaced apart openings, and said rods extend through a respective opening in said support bar.

49. The apparatus of claim 47, wherein first and second brackets have an elongated slot and said ends of said support bar include a bearing member received in said slot in said first bracket and second bracket, respectively wherein said bearing members of said arm slide within said slots as said first support moves along said linear path.

50. An apparatus for unloading a gel from an isoelectric focusing gel tube, said apparatus comprising:
- a housing having a first end, a second end opposite said first end and a side wall, said housing having an axial passage extending between said first and second ends, said axial passage having a first open end at said first end of said housing and a second open end at said second end of said housing;
- a plunger rod having a first end positioned in said first open end of said axial passage of said housing;
- a gel tube having an axial bore containing an isoelectric focusing gel, said gel tube having a first open axial end and a second open axial end, said first open axial end of said gel tube being positioned in said second open end of said axial passage; and
- a resilient plunger member positioned between said first end of said plunger rod and said gel within said gel tube, said resilient plunger member having an outer dimension to fit within said bore of said gel tube.

51. The apparatus of claim 50, wherein said plunger member is a resilient rubber ball having an outer dimension slightly greater than an inner dimension of said gel tube.

52. The apparatus of claim 50, wherein said plunger rod has a substantially cylindrical shape and an outer dimension to slide within said gel tube.

53. The apparatus of claim 52, wherein said plunger rod includes an actuator member coupled to said second end thereof.

54. A method of unloading an isoelectric focusing gel from a gel tube, said method comprising:
- providing a gel tube having an axial bore containing an isoelectric focusing gel, said gel tube having a first open axial end and a second open axial end;
- coupling said first end of said gel tube to a first end of an unloading assembly, said unloading assembly having a flexible plunger member aligned with said first open axial end of said gel tube and a reciprocating plunger rod aligned with said plunger member and said first open axial end of said gel tube; and
- moving said plunger rod against said plunger member and forcing said plunger member and said first end of said plunger rod through said axial passage of said gel tube to unload said gel.

55. The method of claim 54, wherein said plunger rod is a substantially rigid rod having a substantially cylindrical shape.

56. The method of claim 55, wherein said plunger rod includes an actuator member coupled to said second end thereof, and wherein said method comprises actuating said actuator member to unload said gel.

57. The method of claim 54, wherein said plunger member is a substantially spherical silicone rubber member having an outer dimension greater than an inner diameter of said gel tube so as to deform as said plunger member passes through said gel tube.

58. The method of claim 54, further comprising
- providing a drive assembly coupled to said plunger rod, and
- actuating said drive assembly to move said plunger rod and plunger member through said gel tube.

59. The method of claim 58, further comprising providing a plurality of said gel tubes and a plurality of said plunger members and plunger rods, each of said plunger members and plunger rods being aligned with a respective gel tube, and where each of said plunger rods are coupled to said drive assembly for simultaneously moving said plunger rods and plunger members through said gel tubes.

* * * * *

UNITED STATES PATENT AND TRADEMARK OFFICE
CERTIFICATE OF CORRECTION

PATENT NO. : 6,783,648 B1  
DATED : August 31, 2004  
INVENTOR(S) : Anderson et al.

Page 1 of 1

It is certified that error appears in the above-identified patent and that said Letters Patent is hereby corrected as shown below:

Column 1,  
Line 13, the following information should be inserted:  
-- This invention was made with United States Government support under cooperative agreement number 70NANB5H1075 awarded by the National Institute of Standards and Technology. The government has certain rights in the invention. --.  
Line 19, delete "condons" and insert -- codons --.

Column 14,  
Line 36, delete "apparatus,of" and insert -- apparatus of --.

Column 16,  
Line 24, delete "The,apparatus" and insert -- The apparatus --.

Signed and Sealed this

Twenty-fifth Day of October, 2005

JON W. DUDAS  
*Director of the United States Patent and Trademark Office*